(12) United States Patent
Lavoritano et al.

(10) Patent No.: US 11,141,197 B2
(45) Date of Patent: Oct. 12, 2021

(54) POLYAXIAL STRUT FOR EXTERNAL FIXATION

(71) Applicant: DEPUY SYNTHES PRODUCTS, INC., Raynham, MA (US)

(72) Inventors: Scott Lavoritano, West Chester, PA (US); Joseph Costanzo, West Chester, PA (US); Joseph Peterson, Raynham, MA (US); Michael Wahl, West Chester, PA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 95 days.

(21) Appl. No.: 16/450,527

(22) Filed: Jun. 24, 2019

(65) Prior Publication Data
US 2020/0397480 A1 Dec. 24, 2020

(51) Int. Cl.
*A61B 17/62* (2006.01)
*A61B 17/64* (2006.01)
*A61B 17/60* (2006.01)

(52) U.S. Cl.
CPC .......... *A61B 17/6416* (2013.01); *A61B 17/62* (2013.01); *A61B 17/6408* (2013.01); *A61B 2017/606* (2013.01)

(58) Field of Classification Search
CPC .................. A61B 2017/606; A61B 2017/0042
See application file for complete search history.

(56) References Cited

U.S. PATENT DOCUMENTS

| | | | |
|---|---|---|---|
| 2,334,039 A | 11/1943 | Rueb | |
| 2,526,105 A | 10/1950 | Adams | |
| 4,530,261 A | 7/1985 | Ventura | |
| 6,105,473 A | 8/2000 | Huang | |
| 7,087,057 B2 | 8/2006 | Konieczynski et al. | |
| 7,430,943 B2 | 10/2008 | Chiang | |
| 7,699,876 B2 * | 4/2010 | Barry | A61B 17/7037 606/266 |
| 7,867,258 B2 | 1/2011 | Drewry et al. | |
| 7,942,426 B2 | 5/2011 | Peters | |
| 8,250,949 B2 | 8/2012 | Hu | |
| 8,663,291 B2 | 3/2014 | Doubler et al. | |
| 8,945,128 B2 | 2/2015 | Singh et al. | |
| 9,220,533 B2 | 12/2015 | Singh et al. | |

(Continued)

FOREIGN PATENT DOCUMENTS

| | | |
|---|---|---|
| EP | 3 245 966 A1 | 11/2017 |
| WO | 2009/1 00459 | 8/2009 |

OTHER PUBLICATIONS

Patent Cooperation Treaty International Search Report dated Jun. 24, 2019.

*Primary Examiner* — Pedro Philogene
(74) *Attorney, Agent, or Firm* — Kramer Amado

(57) ABSTRACT

A polyaxial external fixation strut including a strut member and a first ball joint coupled to an end portion of the strut member. The first ball joint includes a first ball joint body and a first ball member. The first ball member is rotatably coupled to the first ball joint body to allow for variable angle adjustable positioning of the first ball member within the first ball joint body. The first ball joint additionally includes a friction member. The friction member is configured to create friction between the first ball member and the first ball joint body.

22 Claims, 22 Drawing Sheets

(56) References Cited

U.S. PATENT DOCUMENTS

| | | |
|---|---|---|
| 9,730,730 B2 | 8/2017 | Singh et al. |
| 9,833,263 B2 | 12/2017 | Chandanson et al. |
| 9,839,445 B2 | 12/2017 | Singh et al. |
| 2016/0066956 A1* | 3/2016 | Siemer .................. A61B 17/62 606/56 |
| 2016/0270822 A1* | 9/2016 | Cresina ................ A61B 17/645 |
| 2018/0368887 A1 | 12/2018 | Lauf et al. |
| 2019/0021767 A1 | 1/2019 | Singh et al. |
| 2019/0029727 A1 | 1/2019 | Park et al. |

\* cited by examiner

POLYAXIAL STRUT FOR EXTERNAL FIXATION

BACKGROUND OF THE INVENTION

1. Field of the Invention

This disclosure relates generally to polyaxial struts for external bone fixation. More particularly, this disclosure relates generally to polyaxial struts including structures that maintain the ends of the polyaxial struts in an adjustable position.

2. Description of Related Art

External fixation traditionally entails the use of percutaneously placed pins and/or wires secured to an external scaffolding device to provide support for a fractured limb. Using this mechanism, a bone or joint can be stabilized during limb reconstruction. The technique presents many benefits compared to internal plates and intramedullary nails. External fixators cause less disruption of soft tissues, osseus blood supply and periosteum and are especially ideal for soft tissue management in cases of acute or chronic trauma wherein skin quality is compromised. Additionally, the temporary nature of the pins and wires make frames ideal for providing bone stability in cases of infection of the bone, where the presence of internal implants would make treatment of the infection more challenging. Furthermore, unlike internal plates, external fixators provide postoperative adjustability. External fixation may also be used in limb lengthening and deformity correction procedures.

Various types of external fixators are used for clinical applications. One type of external fixator is a circular frame fixator. The classic circular frame is the Ilizarov external fixator that may be integrated with other circular frames, such as the Taylor Spatial Frame (TSF). The basic components of the frame are rings, connecting rods, and struts. Ilizarov rings may be configured as full (closed) rings, partial (open) rings, or arches.

Another type of circular frame is the Taylor Spatial Frame (TSF). The TSF is a hexapod device based on a Stewart platform. The device includes two or more aluminum or carbon fiber rings connected by struts. Each strut can be independently lengthened or shortened to achieve the desired result, i.e., compression at the fracture site, lengthening, etc. The TSF is connected to the bone by wires or half pins, and the attached bone may be manipulated in six axes (anterior/posterior, varus/valgus, lengthen/shorten).

Polyaxial struts are commonly used to create external fixation frames in which the struts are not necessarily parallel to each other and are not necessarily perpendicular to the rings. Typical strut ends swivel to accommodate non-orthogonal orientations, and such swiveling ends are commonly unconstrained during frame construction such that they default to whatever relative position is governed by gravity. In order to ease the process of building such frames, it is desirable for these polyaxial strut swivels to maintain the orientation set by the surgeon, rather than what is set by gravity, during frame construction. It is also desirable to be able to fix the strut angulation prior to fixing the strut to the ring.

Additionally, two different types of struts exist in the marketplace for strut ring fixator frames: linear struts and polyaxial struts. This creates an added cost for manufacturers and reduced flexibility for surgeons. Accordingly, a strut configured to behave as a linear and a polyaxial strut is also desirable.

SUMMARY OF THE INVENTION

The foregoing advantages of the invention are illustrative of those that can be achieved by the various exemplary embodiments and are not intended to be exhaustive or limiting of the possible advantages that can be realized. Thus, these and other objects and advantages of the various exemplary embodiments will be apparent from the description herein or can be learned from practicing the various exemplary embodiments, both as embodied herein or as modified in view of any variation that may be apparent to those skilled in the art. Accordingly, the invention resides in the novel methods, arrangements, combinations, and improvements herein shown and described in various exemplary embodiments.

In light of the present need for polyaxial external fixation strut systems having more constrained swivel ends, a brief summary of various exemplary embodiments is presented. Some simplifications and omissions may be made in the following summary, which is intended to highlight and introduce some aspects of the various exemplary embodiments, but not to limit the scope of the invention. Detailed descriptions of a preferred exemplary embodiment adequate to allow those of ordinary skill in the art to make and use the inventive concepts will follow in later sections.

Various embodiments herein relate to a polyaxial external fixation strut including a strut member and a first ball joint coupled to an end portion of the strut member. The first ball joint includes a first ball joint body and a first ball member. The first ball member is rotatably coupled to the first ball joint body. The first ball joint additionally includes a friction member, such as a spring clip member or spring member, configured to create friction between the first ball member and the first ball joint body to maintain an adjustable position of the first ball member relative to the first ball joint body.

Various embodiments disclosed herein relate to a polyaxial external fixation strut including a strut member and a first ball joint coupled to an end portion of the strut member. The first ball joint includes a first ball joint body and a first ball member. The first ball member is rotatably coupled to the first ball joint body. The first ball joint additionally includes a channel that runs along at least a partial circumference of an inner surface of the first ball joint body or a channel that runs along at least a partial circumference of the outer surface of the first ball member, configured to accommodate a friction member, such as a spring clip or a spring member. The friction member is configured to create friction between the first ball member and the first ball joint body to maintain an adjustable position of the first ball member relative to the first ball joint body.

Various embodiments disclosed herein additionally relate to polyaxial external fixation struts, wherein the strut member additionally includes a second ball joint coupled to an end portion of the strut member opposite the first ball joint.

Various embodiments herein additionally relate to polyaxial external fixation struts including a spring member, wherein the spring member includes a conical spring washer.

Various embodiments disclosed herein additionally relate to polyaxial external fixation struts including a spring clip member, wherein the spring clip member is C-shaped.

Various embodiments disclosed herein additionally relate to polyaxial external fixation struts further including a first ring contact portion attached to the first ball member.

Various embodiments disclosed herein additionally relate to polyaxial external fixation struts further including a fixator clip attached to the first ball joint body and first ring contact portion and configured to fix the first ball joint body and first ring contact portion in a linear configuration.

BRIEF DESCRIPTION OF THE DRAWINGS

In order to better understand various exemplary embodiments, reference is made to the accompanying drawings, wherein.

DETAILED DESCRIPTION OF THE INVENTION

Embodiments described herein disclose a polyaxial external fixation strut. Various embodiments herein additionally disclose permanent and temporary devices that allow for constrained polyaxial as well as linear functionality of the external fixation strut. The various embodiments disclosed herein allow for a surgeon to maintain an angular orientation of a swiveling end of a polyaxial strut during external frame construction.

Figure 1:
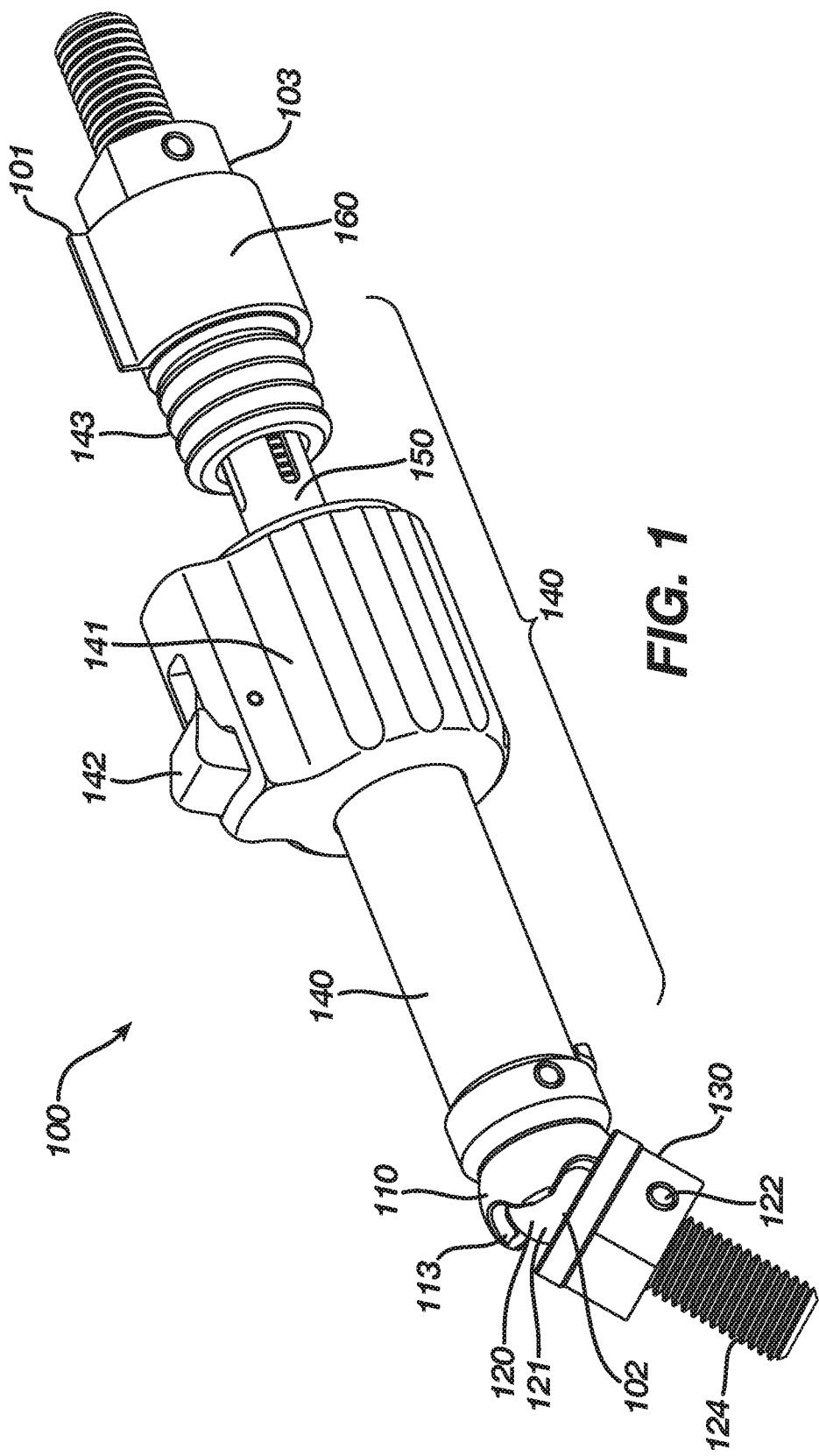
FIG. 1 illustrates a perspective side view of the polyaxial strut.
Figure 2:
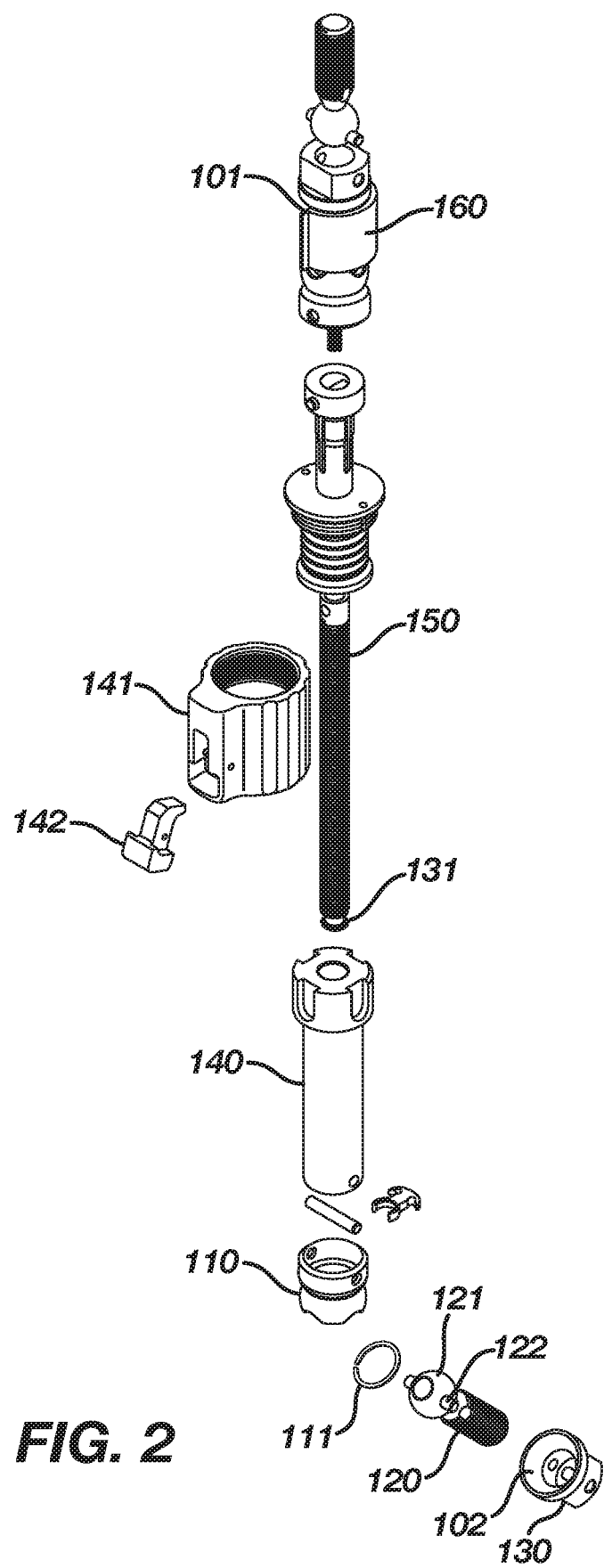
FIG. 2 illustrates an exploded view of the polyaxial strut.

Referring now to the drawings, in which like numerals refer to like components or steps, there are disclosed broad aspects of various exemplary embodiments. FIGS. 1 and 2 illustrate a perspective side view and exploded view, respectively, of an embodiment of the polyaxial strut 100. The polyaxial strut 100 includes a proximal ball joint 101 and a distal ball joint 102. The proximal ball joint 101 and distal ball joint 102 both may include a ball joint body 110 and a ball joint stud member 120 rotatably coupled to the ball joint body 110. The ball joint stud member 120 includes a ball member 121 and a shaft portion 124. As shown in FIG. 1, the ball joint body 110 includes a plurality of grooves 113 configured to accommodate the proximal end of the shaft portion 124 of the ball joint stud member 120. The grooves 113 allow for acute angulation of the ball joint stud member 120 within the ball joint body 110 at specific angular positions as set by the surgeon. The distal ball joint 102 additionally includes a ring contact portion 130 that is attached to the ball joint stud member 120 using a pin 122 configured to inhibit rotation of the ball joint stud member 120 within the ring contact portion 130.

The polyaxial strut 100 further includes a strut member 140 that includes a strut tube 141 that slidably receives a strut rod 150. The strut tube 141 and strut rod 150 are connected using a connecting portion 142, which includes an adjustment knob 143. The adjustment knob 143 is configured to allow for length adjustment of the polyaxial strut 100 to the desired length to fit a ring frame (not shown) used for external fixation. In this embodiment, depression of the adjustment knob 143 allows slidable movement of the strut rod 150 within the strut tube 141. However, the adjustment knob 143 may include any configuration known in the art that would allow for length adjustment of the polyaxial strut 100. As shown in FIG. 2, the distal ball joint 102 may further include a spring clip member 111 that is configured to at least partially surround the ball member 121 of the ball joint stud member 120.

Additionally, as shown in FIG. 1, a fixator clip member 160, described in more detail below, may be attached to the proximal ball joint 101 and/or distal ball joint 102 in order to fix the ball joints 101, 102 in a linear configuration.

Figure 3:
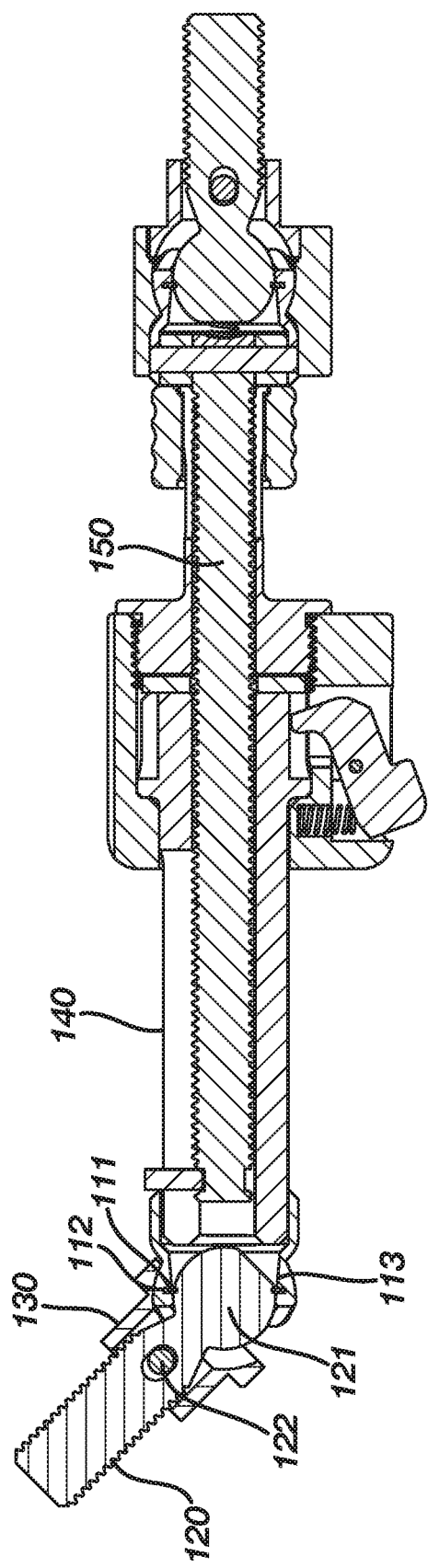
FIG. 3 illustrates a cross-sectional side view of the polyaxial strut.

FIG. 3 shows a cross-sectional side view of the polyaxial strut 100. As shown in FIG. 3, the ball joint body 110 may include a channel 112 that runs along a circumference of an inner surface 113 of the ball joint body 110. The channel 112 is configured to accommodate the spring clip member 111. The ball member 121 may also include a channel 125 to accommodate the spring clip member 111. As shown in FIG. 3, the spring clip member 111 is configured to create friction between the ball member 121 as it is rotated in the ball joint body 110 to maintain an adjustable position of the ball member 121 within the ball joint body 110.

Figure 4:
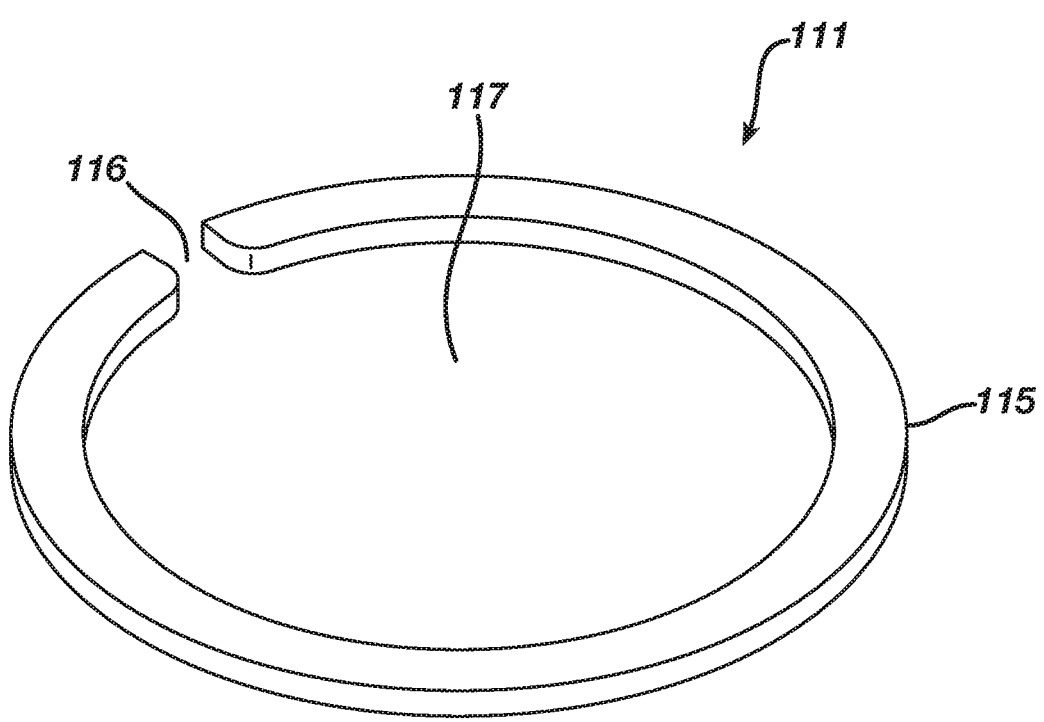
FIG. 4 illustrates a perspective view of a spring clip member.
Figure 5:
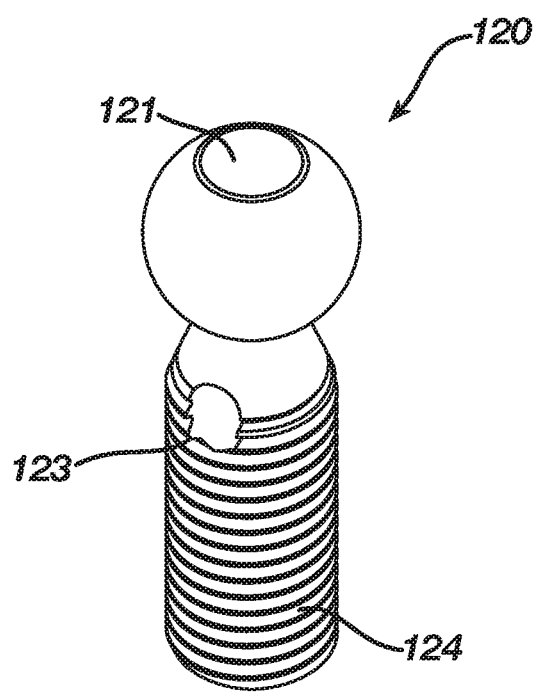
FIG. 5 illustrates a side view of the ball joint stud member.

FIG. 4 shows a more detailed view of an embodiment of the spring clip member 111. In this embodiment, the spring clip member 111 includes a C-shaped edge 115 with an open side 116 and a central opening 117. FIG. 5 shows a more detailed view of an embodiment of the ball joint stud member 120. The ball joint stud member 120 includes a ball member 121 at a proximal end, and an aperture 123 to accommodate the pin 122 that attaches the ball joint stud member 120 to the ring contact portion 130. The ball joint stud member 120 additionally may include a threaded shaft portion 124 configured to secure the polyaxial strut 100 to an external fixation frame (not shown).

Figure 6:
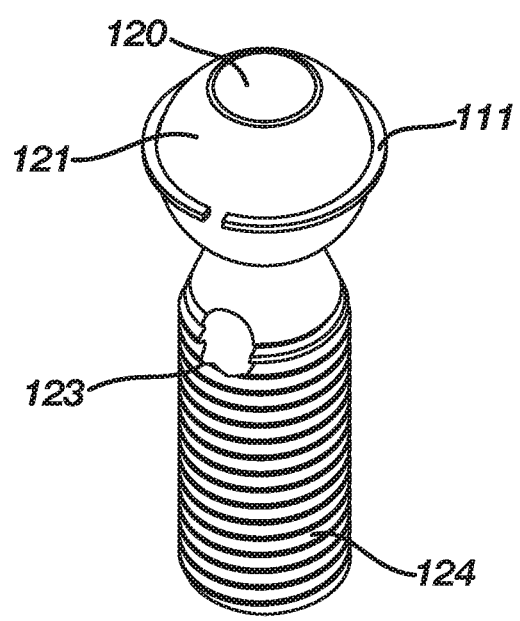
FIG. 6 illustrates movement of the ball joint stud member relative to the spring clip member.

FIG. 6 shows a more detailed view of an embodiment of the spring clip member 111 partially surrounding the ball member 121 of the ball joint stud member 120. As shown, the ball member 121 is configured to fit snugly within the central opening 117 of the spring clip member 111.

Figure 7:
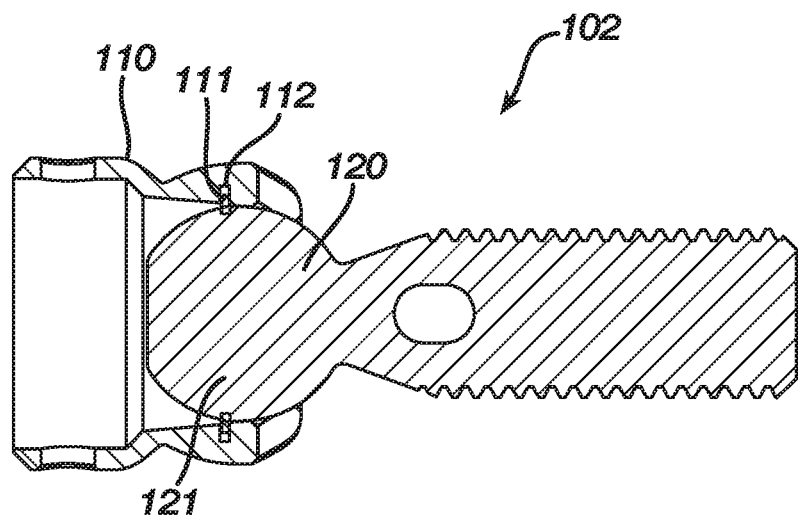
FIG. 7 illustrates a cross-sectional side view of the ball joint stud member and spring clip member positioned in the ball joint body in a linear configuration.
Figure 8:
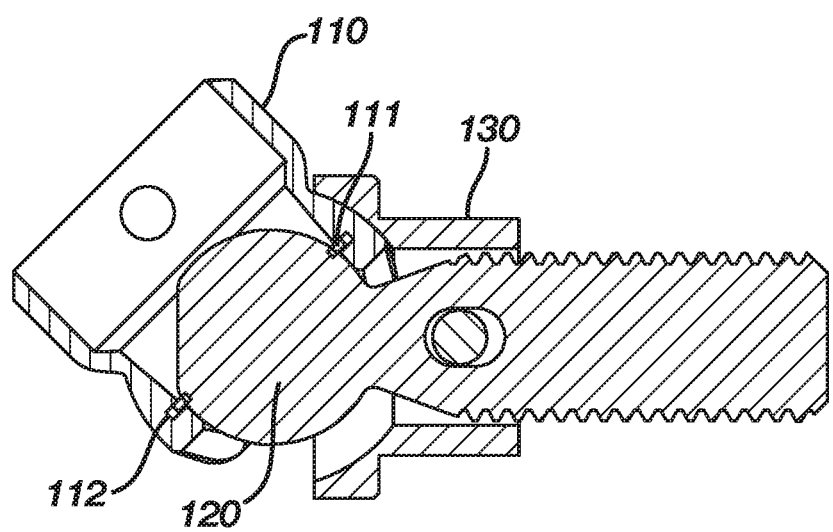
FIG. 8 illustrates a cross-sectional side view of the ball joint stud member and spring clip member positioned in the ball joint body and ball joint ring contact in an angled configuration.

FIG. 7 illustrates a more detailed cross-sectional side view of the distal ball joint 102. As shown in the FIG. 7, the ball joint body 110 includes the channel 112 sized to accommodate the spring clip member 111. The ball member 121 of the ball joint stud member 120 is rotatably accommodated by the spring clip member 111. In use, the ball joint stud member 120 may be moved by the surgeon within the spring clip member 111. The spring clip member 111 is configured to create friction between the ball member 121 and the ball joint body 110 as the ball member 121 is rotated in the ball joint body 110 to maintain an adjustable position of the ball member 121 within the ball joint body 110, as more clearly shown in FIG. 8.

In other embodiments, the spring clip member 111 may be integrated into any layer of the distal ball joint 102, or in multiple layers of the distal ball joint 102. In some embodiments, the spring clip member 111 may sit in a groove on the ball member 121 to interface with an inner surface of the ball joint body 110. In various embodiments, the amount of friction created by the spring clip member 111 may be a function of the contact surface coefficient and any normal forces created by the spring clip member 111. The surface finishes and spring constants of the spring clip member 111 may be optimized according to the amount of fixation desired as known by those of skill in the art.

Figure 9A:
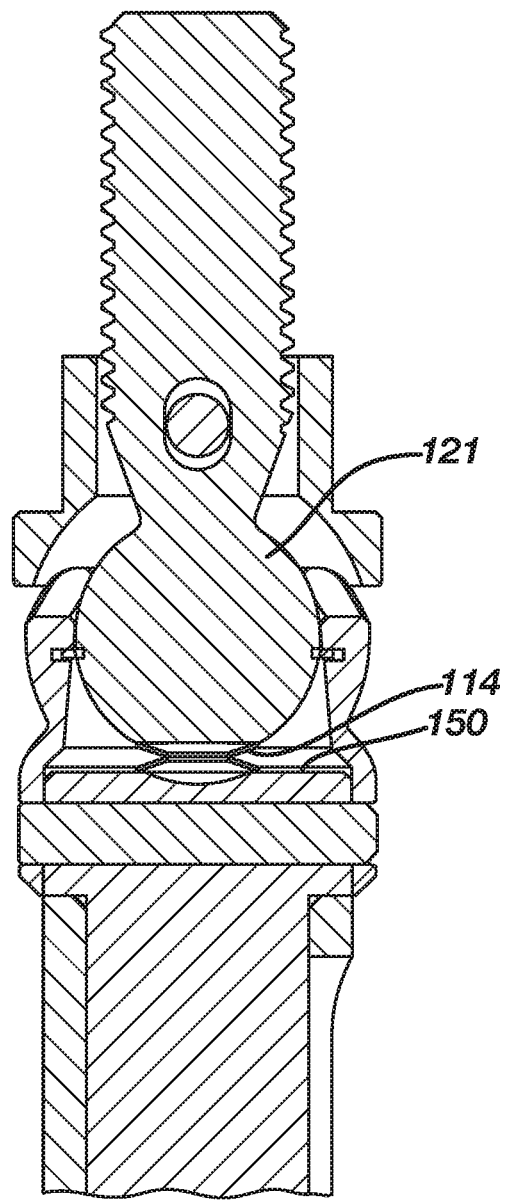
FIG. 9A illustrates a cross sectional side view of an end of the polyaxial strut having a spring member positioned between the strut rod and the ball joint stud member.
Figure 9B:
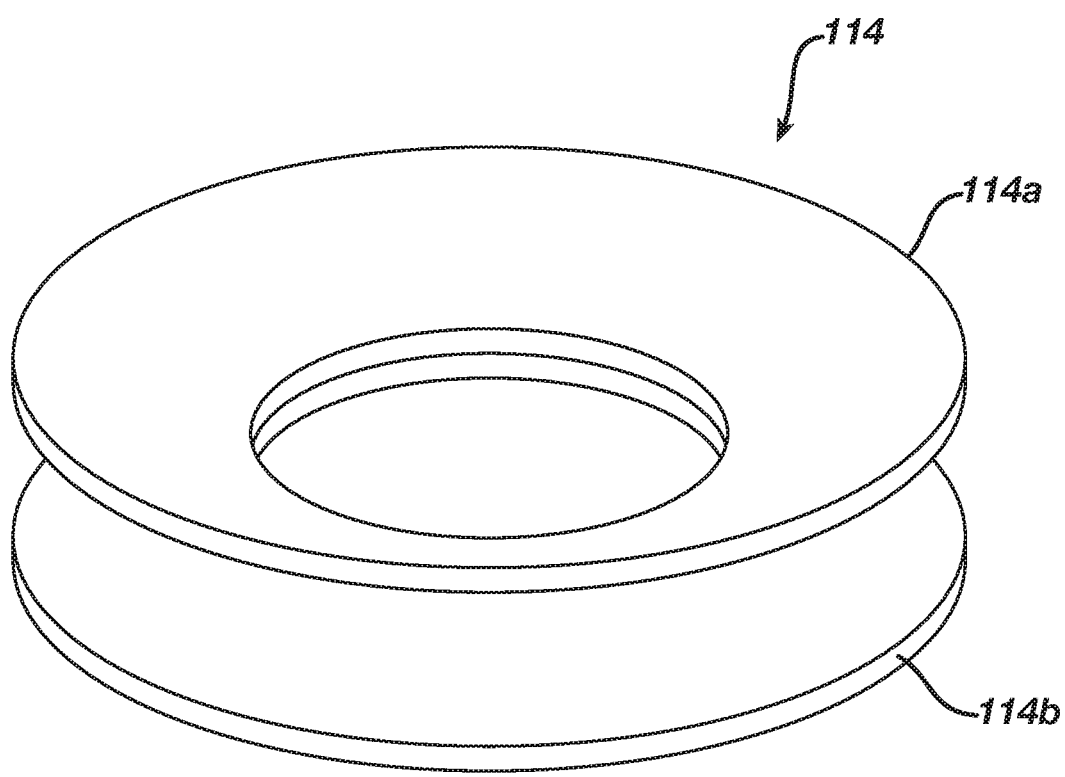
FIG. 9B illustrates a perspective view of the spring member.

In alternative embodiments, the spring clip member 111 may be replaced by any device that effectively creates friction between the ball member and the ball joint body. In various embodiments, the friction-creating member may be a spring member 114, as shown in more detail in FIGS. 9A and 9B. In various embodiments, the spring member 114 may include conical spring washers 114a and 114b, configured to be positioned between an end of the strut rod 150 and the proximal end of the ball member 121.

Figure 10A:
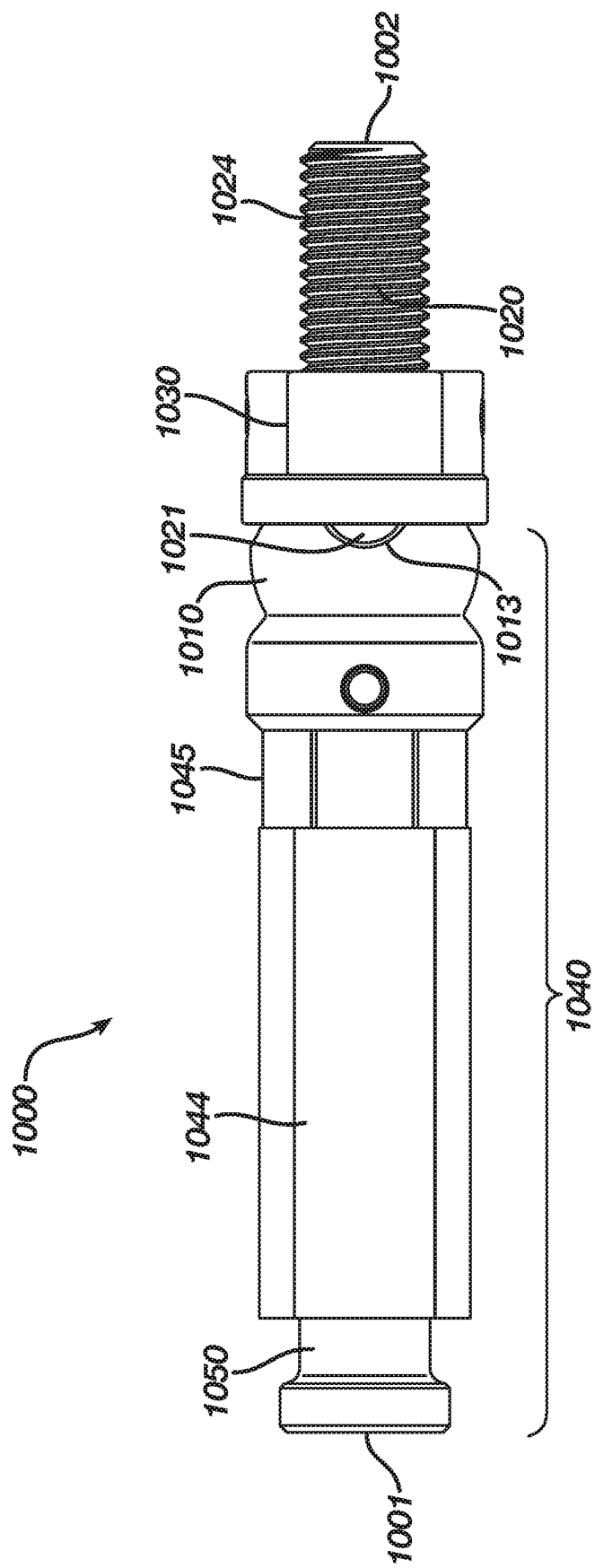
FIG. 10A illustrates a side view of an embodiment of the polyaxial strut configured for use with an external fixator foot support.
Figure 10B:
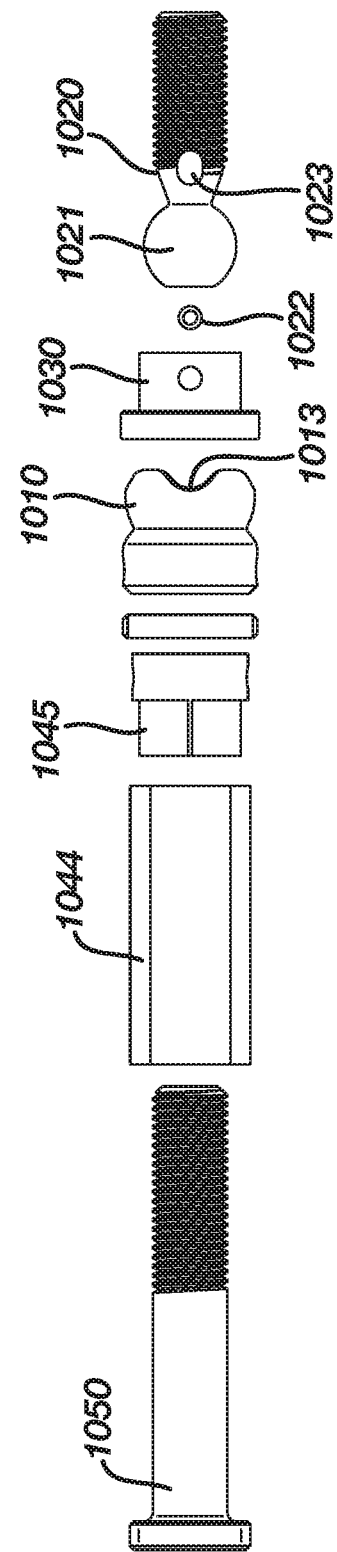
FIG. 10B illustrates an exploded side view of an embodiment of the polyaxial strut configured for use with an external fixator foot support.

FIGS. 10A-10E illustrate a second embodiment of the polyaxial strut 1000. The polyaxial strut 1000 includes a proximal head portion 1001 and a distal ball joint 1002. The distal ball joint 1002 may include a ball joint body 1010 and a ball joint stud member 1020 rotatably coupled to the ball joint body 1010. The ball joint stud member 1020 includes a ball member 1021 and a shaft portion 1024. As shown in FIGS. 10A and 10B, the ball joint body 1010 includes a plurality of grooves 1013 configured to accommodate the proximal end of the shaft portion 1024 of the ball joint stud member 1020. The grooves 1013 allow for acute angulation of the ball joint stud member 1020 within the ball joint body 1010 at specific angular positions as set by the surgeon. The distal ball joint 1002 additionally includes a ring contact portion 1030 that is attached to the ball joint stud member 1020 using a pin 1022 configured to inhibit rotation of the ball joint stud member 1020 within the ring contact portion 1030.

Figure 10C:
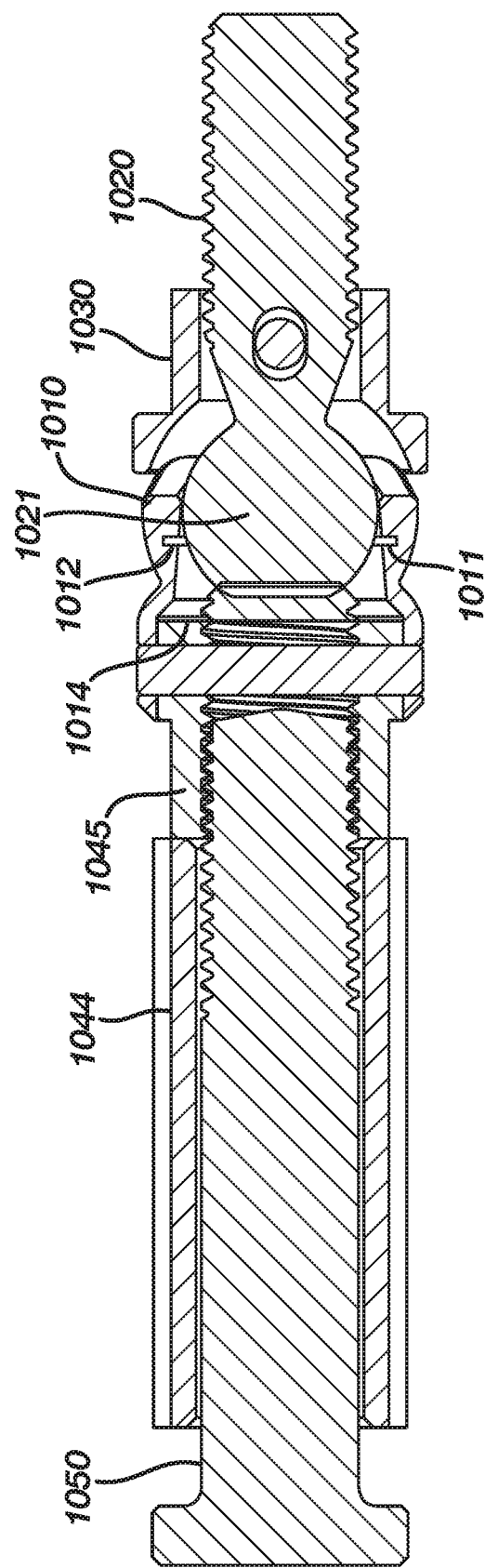
FIG. 10C illustrates a cross-sectional side view of an embodiment of the polyaxial strut configured for use with an external fixator foot support.

The polyaxial strut 1000 further includes a strut member 1040 including a strut bolt 1050 slidably received within a strut housing 1044. The strut bolt is secured to a nut 1045, which is then secured to the ball joint body 1010. As shown in FIG. 10C, the distal ball joint 1002 may further include a spring clip member 1011 that is configured to at least partially surround the ball member 1021 of the ball joint stud member 1020. The ball joint body 1010 may further include a channel 1012 that runs along a circumference of an inner surface 1014 of the ball joint body 1010. The channel 1012 is configured to accommodate the spring clip member 1011. The spring clip member 1011 is configured to create friction between the ball member 1021 as it is rotated in the ball joint body 1010. In alternative embodiments, the spring clip member 1011 may be replaced by any device that effectively creates friction between the ball member and the ball joint body, such as the spring member 114, described herein.

Figure 10D:
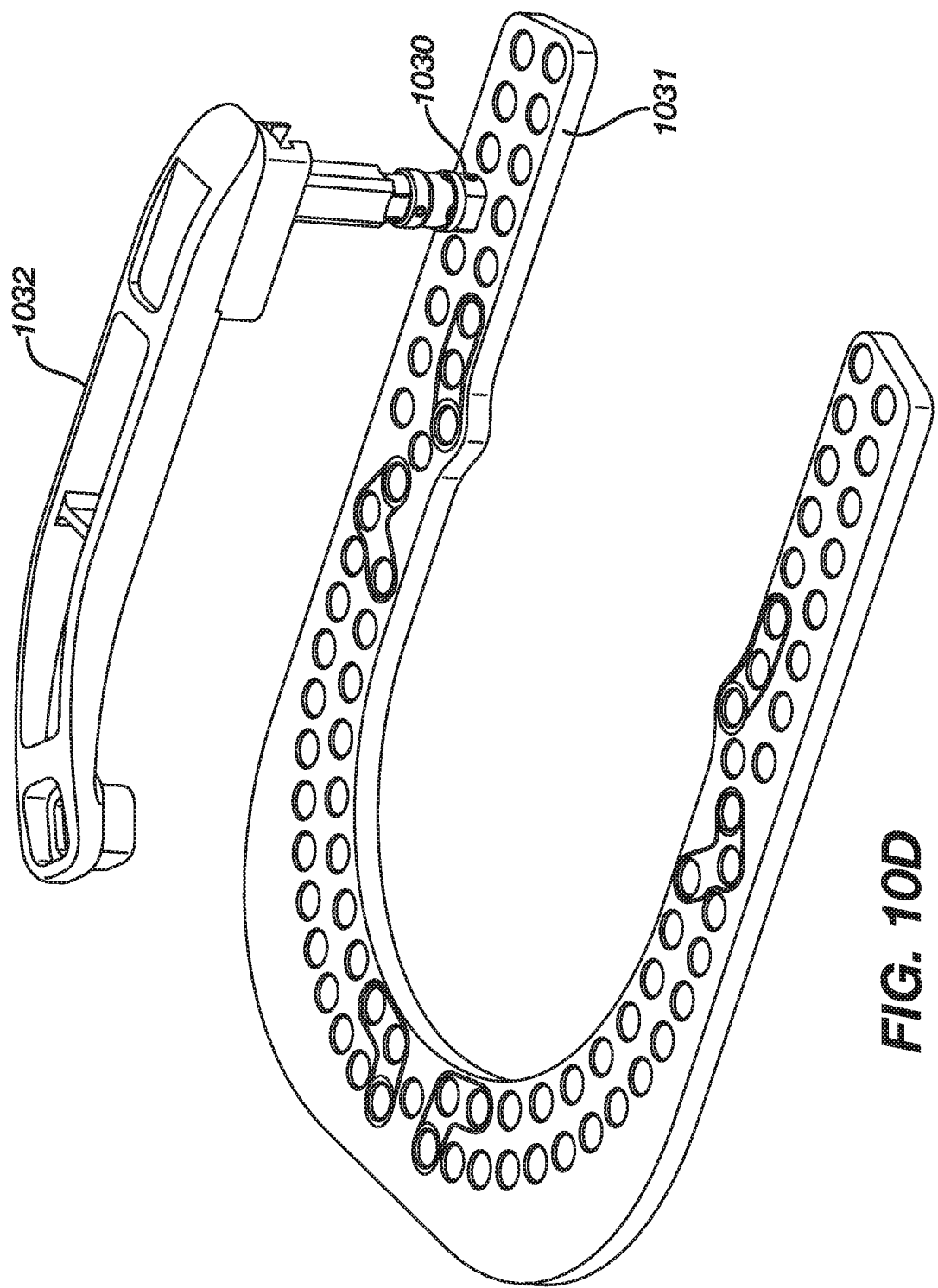
FIGS. 10D and 10E illustrate a perspective and side view of an embodiment of the polyaxial strut mated to an external fixator foot support.
Figure 10E:
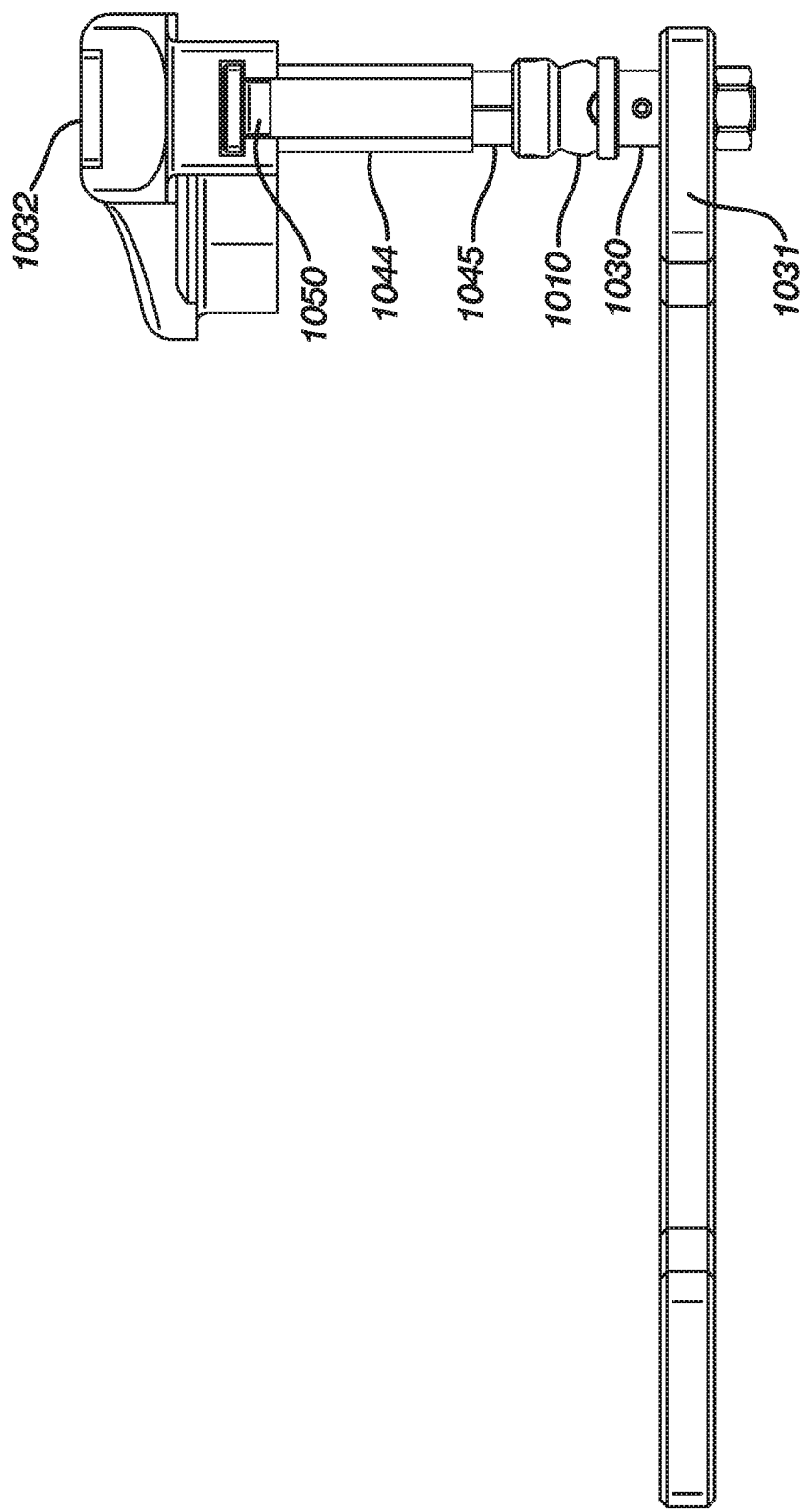

FIGS. 10D and 10E illustrate a perspective and side view of the polyaxial strut 1000 mated to an external fixator foot support frame 1031, 1032.

FIGS. 11A-11D illustrate a third embodiment of the polyaxial strut 1100. The polyaxial strut 1100 includes a proximal head portion 1101 and a distal ball joint 1102. The distal ball joint 1102 may include a ball joint body 1110 and a ball joint stud member 1120 rotatably coupled to the ball joint body 1110. The ball joint stud member 1120 includes a ball member 1121 and a shaft portion 1124. The distal ball joint 1102 additionally includes a ring contact portion 1130 that is attached to the ball joint stud member 1120 using a pin 1122 (shown in FIG. 11D) configured to inhibit rotation of the ball joint stud member 1120 within the ring contact portion 1130.

Figure 11A:
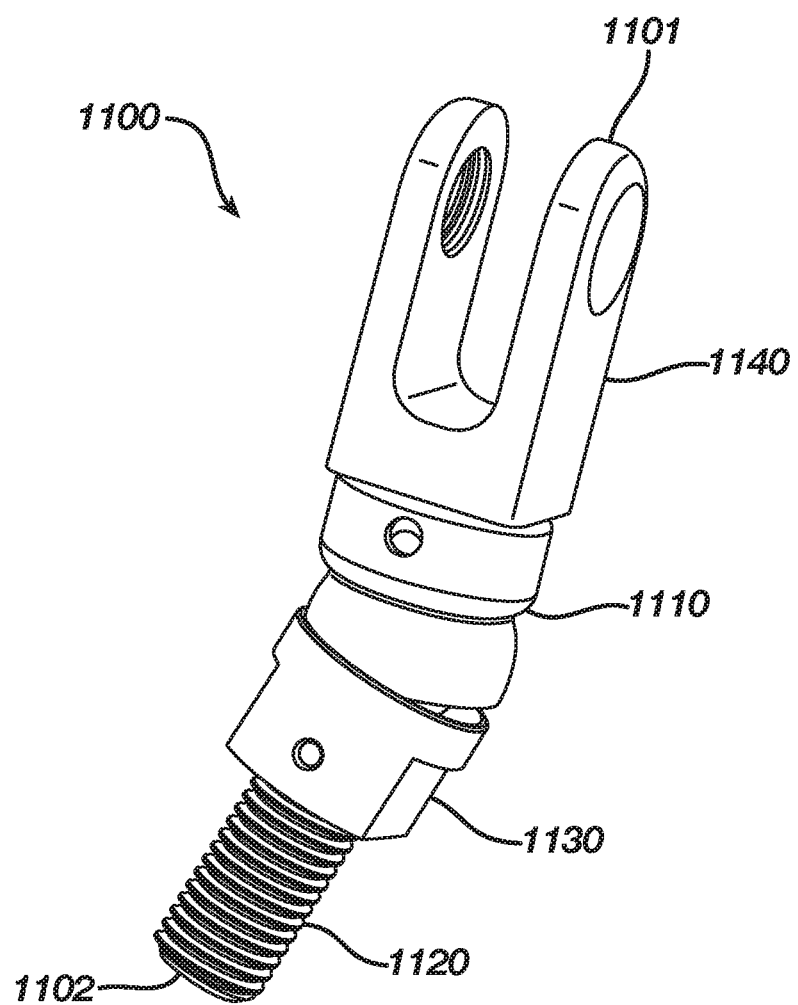
FIG. 11A illustrates a side view of an embodiment of the polyaxial strut configured for use with an external fixator foot plate.
Figure 11B:
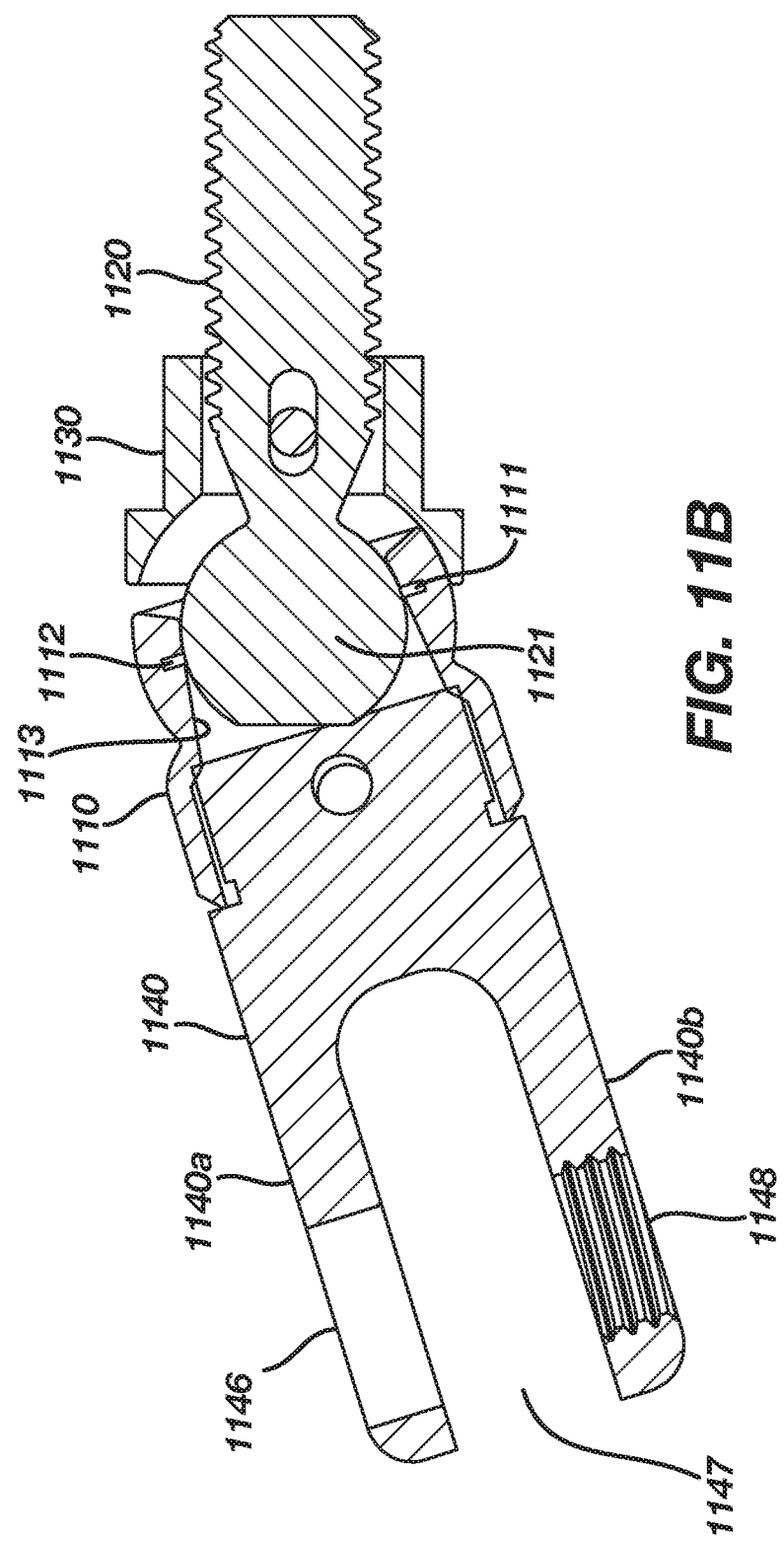
FIG. 11B illustrates a cross-sectional side view of an embodiment of the polyaxial strut configured for use with an external fixator foot plate.
Figure 11C:
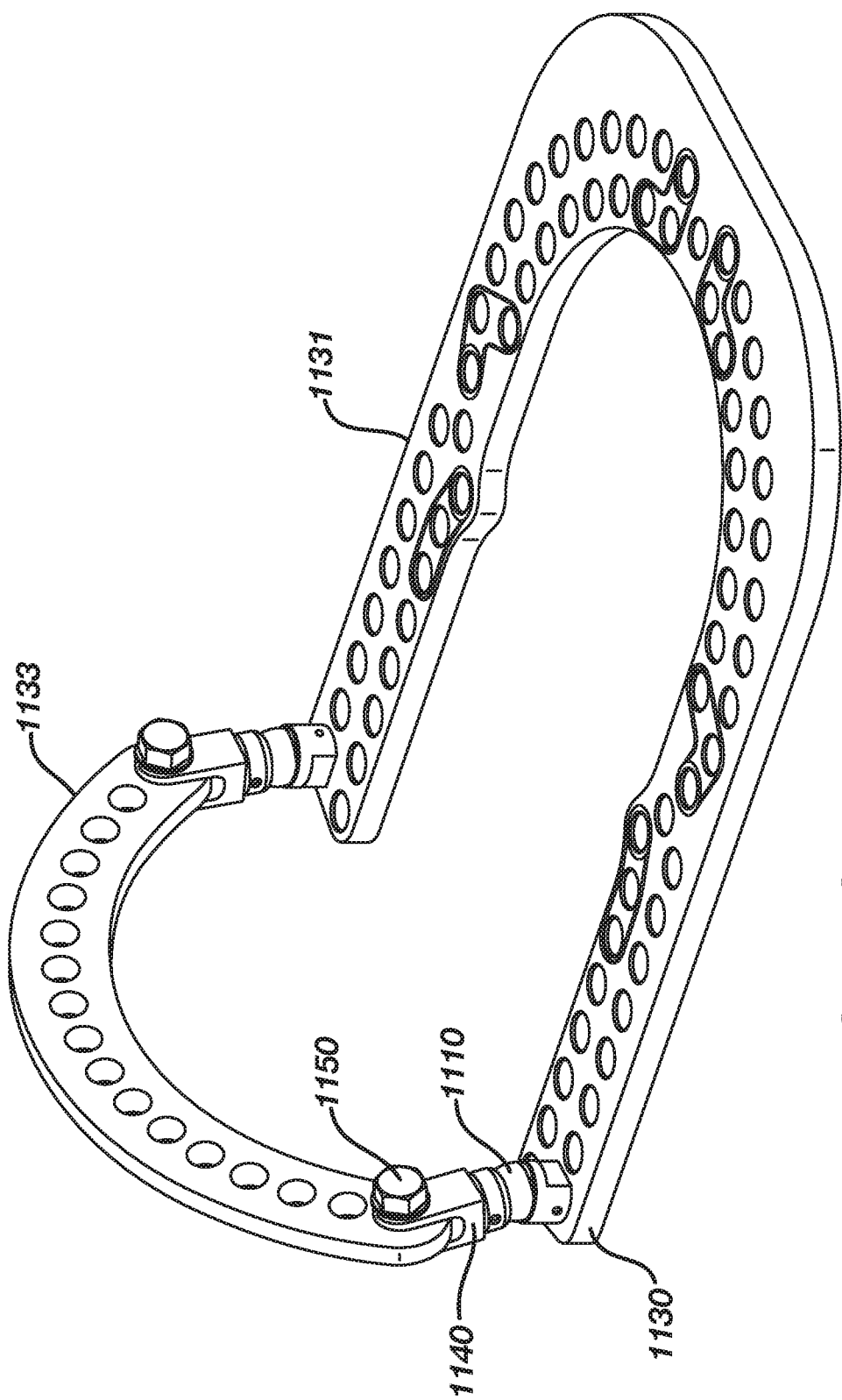
FIGS. 11C and 11D illustrate a perspective and perspective exploded view of an embodiment of the polyaxial strut mated with an external fixator foot plate.
Figure 11D:
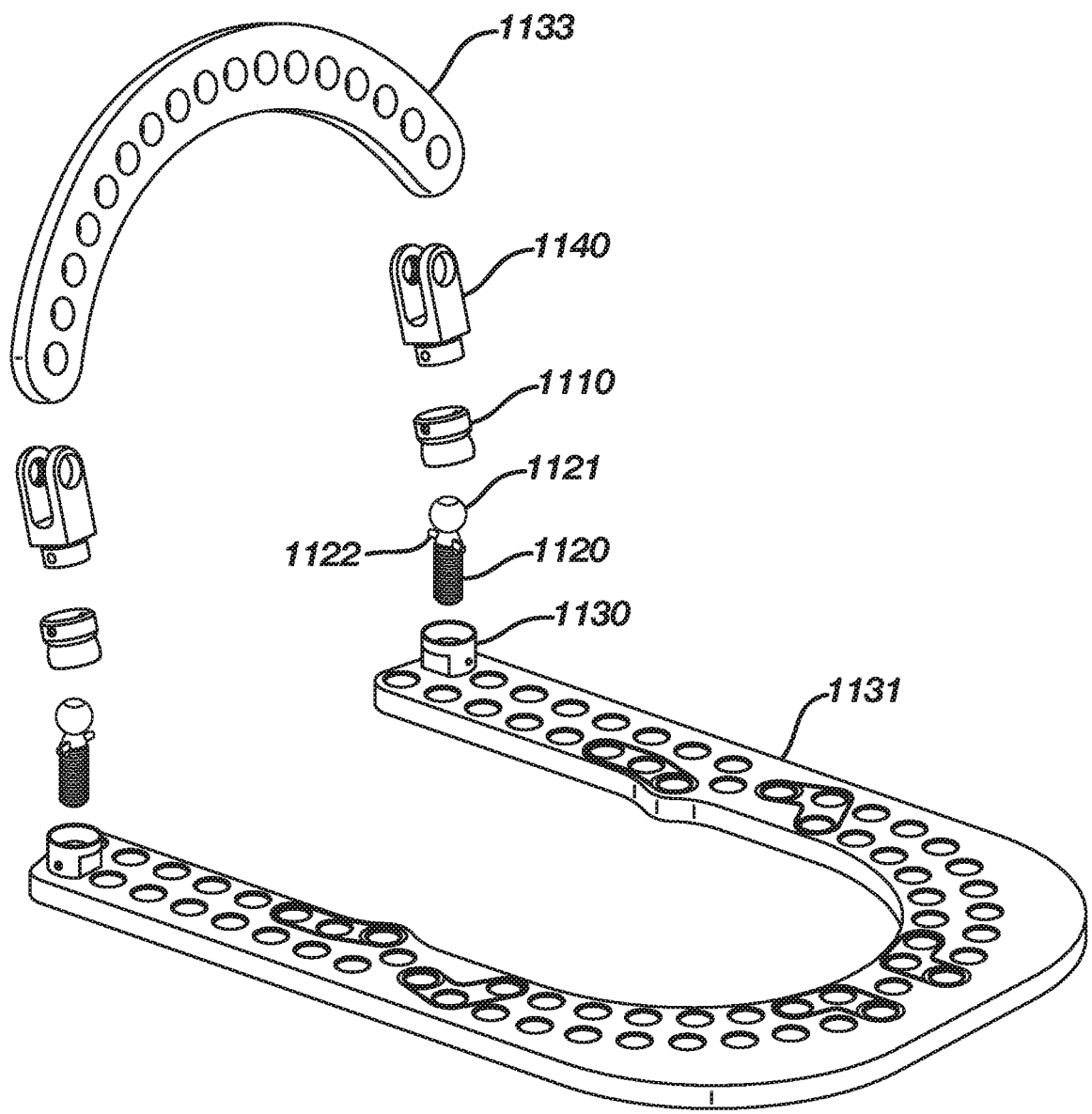

The polyaxial strut 1100 further includes a strut member 1140 including a U-shaped opening 1147 having an unthreaded opening 1146 on first prong 1140a of the U-shape and a threaded opening 1148 on a second prong 1140b of the U-shape. The unthreaded opening 1146 and the threaded opening 1148 are configured to accommodate a bolt 1150, which secures the strut member 1140 to an external fixator foot plate 1131, 1133, as shown in FIG. 11C As shown in FIG. 11B, the distal ball joint 1102 may further include a spring clip member 1111 that is configured to at least partially surround the ball member 1121 of the ball joint stud member 1120. The ball joint body 1110 may further include a channel 1112 that runs along a circumference of an inner surface 1113 of the ball joint body 1110. The channel 1112 is configured to accommodate the spring clip member 1111. The spring clip member 1111 is configured to create friction between the ball member 1121 as it is rotated in the ball joint body 1110. In alternative embodiments, the spring clip member 1111 may be replaced by any device that effectively creates friction between the ball member and the ball joint body, such as the spring member 114, described herein.

Figure 12A:
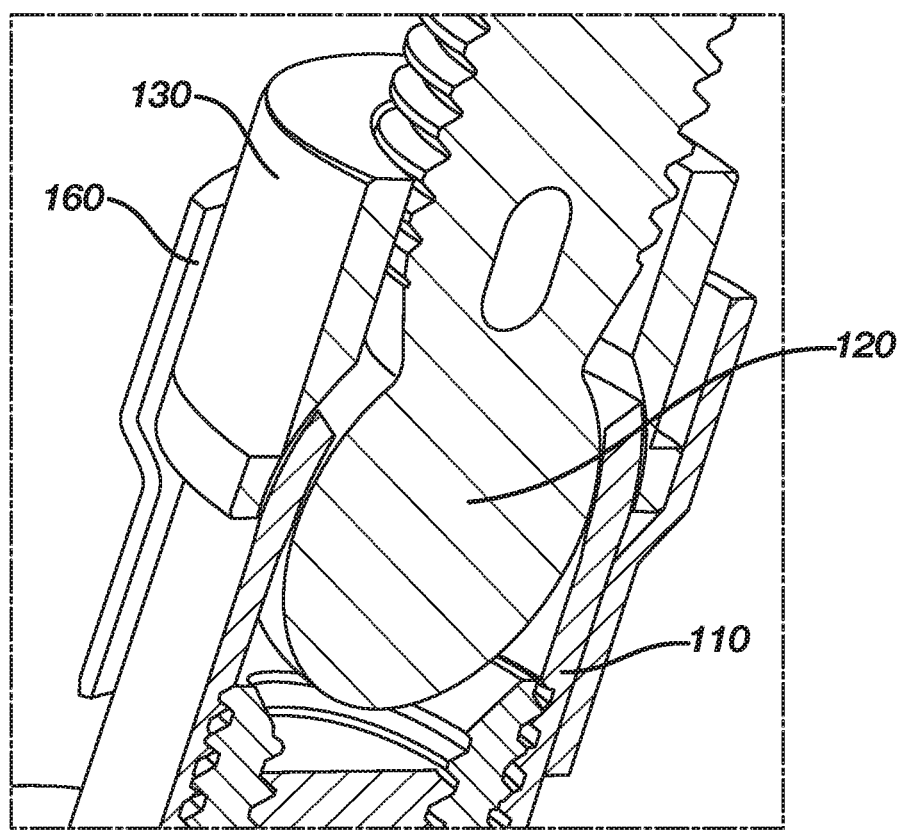
FIG. 12A illustrates a cross-sectional perspective view of the fixator clip attached to the ball joint body and ring contact portion.
Figure 12B:
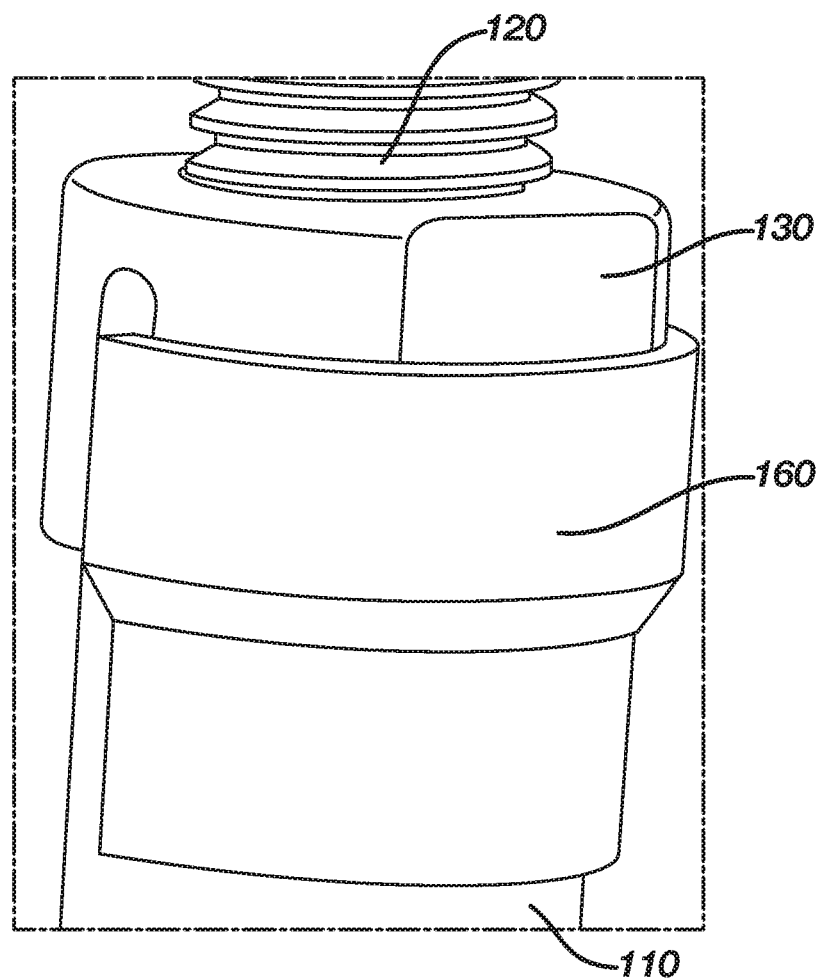
FIG. 12B illustrates a side view of an embodiment of the fixator clip attached to the ball joint body and ring contact portion.
Figure 12C:
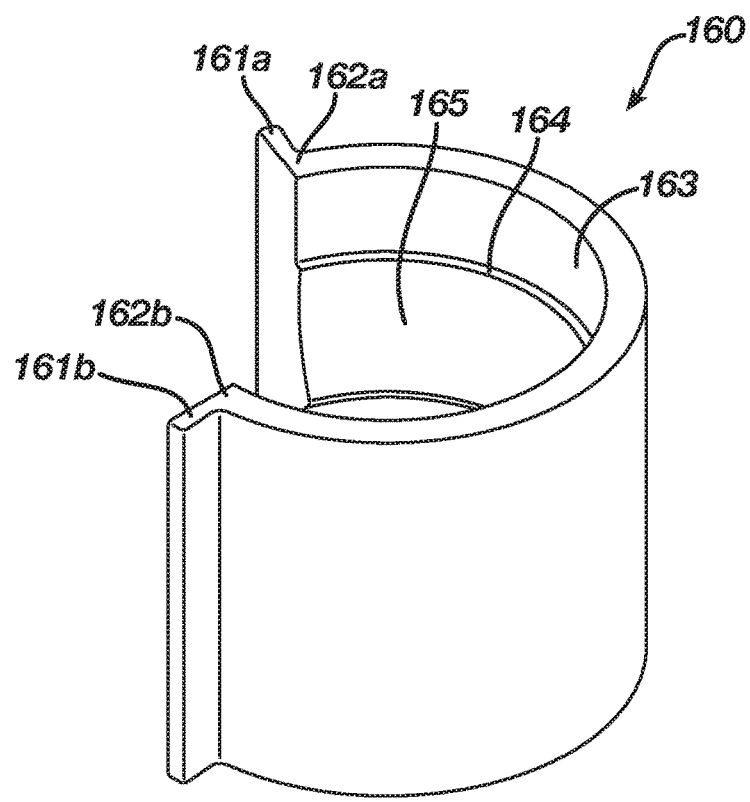
FIGS. 12C and 12D illustrate a perspective and top view, respectively, of the fixator clip.
Figure 12D:
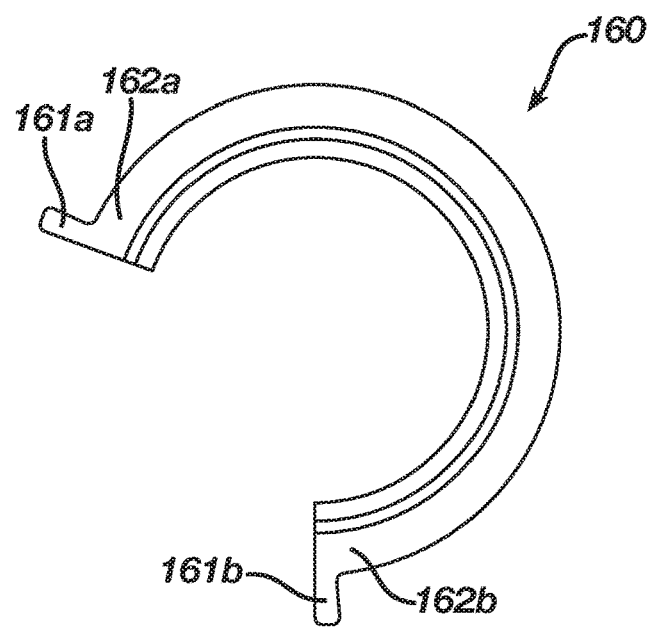
Figure 12E:
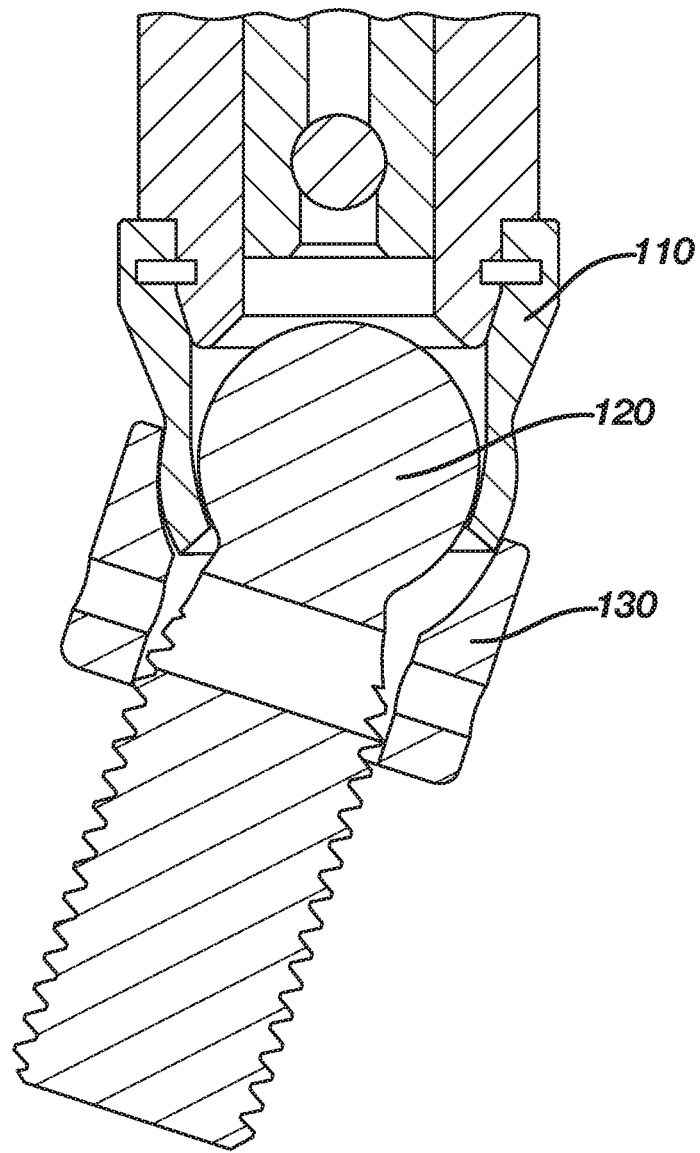
FIG. 12E illustrates a perspective view of the ball joint after removal of the fixator clip.

FIGS. 12A and 12B illustrate a fourth embodiment of the polyaxial strut 100. In this embodiment, the distal ball joint 102 may be further fixed with a removably attached fixator clip 160 that is configured to permanently or temporarily maintain the ball joint body 110, ball joint stud member 120 and ring contact portion 130 in axial alignment during construction of an external fixation device. As shown in FIGS. 12C and 12D, the fixator clip 160 may be substantially C-shaped with outwardly protruding portions 161a, 161b at a first and second tip 162a, 162b of the C shape. In various embodiments, the inner surface 163 of the fixator clip 160 may include ridged portions 164 and concave portions 165 configured to fit snugly over the ball joint body 110 and the ring contact portion 130 in order to permanently or temporarily fix the ball joint body 110, ball joint stud member 120 and ring contact portion 130 in a linear configuration. In use, the fixator clip 160 may be removed at the discretion of the surgeon to allow for angular movement of the distal ball joint 102, as shown in FIG. 12E. The fixator clip 160 may be manufactured from any suitable materials including disposable or reusable plastic or metal materials.

Figure 13:
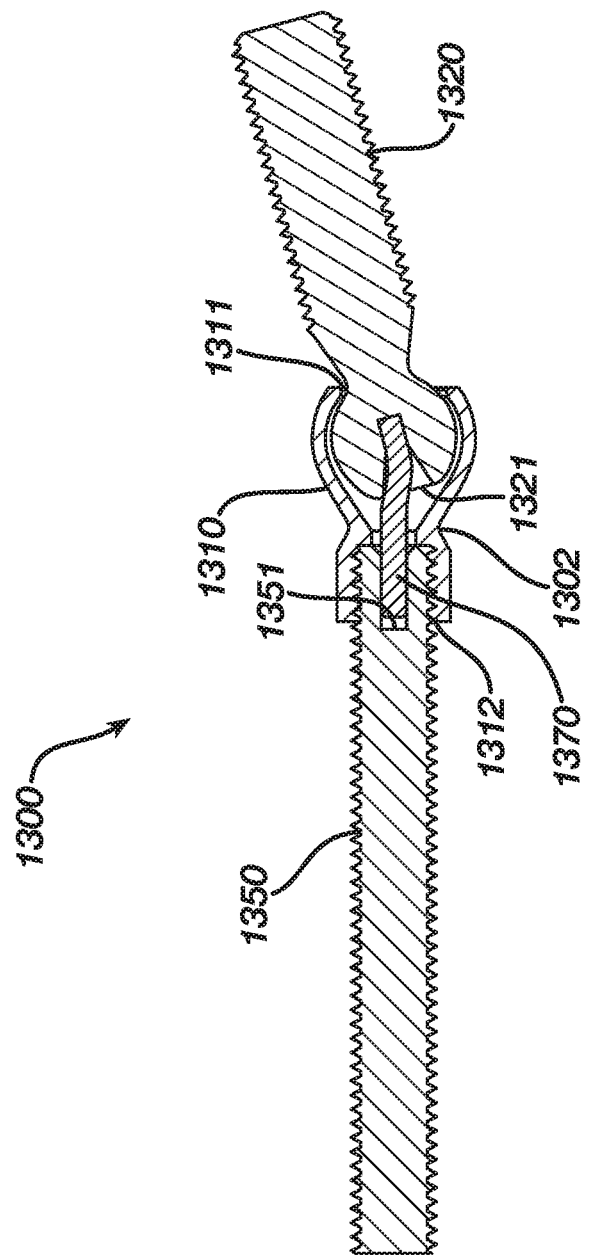
FIG. 13 illustrates a cross-sectional side view of a malleable implant positioned between the strut rod and the ball joint stud member.

FIG. 13 illustrates a fifth embodiment of the polyaxial strut 1300. In this embodiment, the distal ball joint 1302 includes a ball joint body 1310, wherein the ball joint body 1310 includes a first aperture 1311 sized to accommodate a ball joint stud member 1320 at a distal end. The ball joint body 1310 further includes a second aperture 1312 opposite the first aperture 1311 sized to accommodate a strut rod 1350 at a proximal end. In various embodiments, a malleable implant 1370 may be configured to be positioned between the static end 1351 of the strut rod 1350 and the ball joint stud member 1320. The malleable implant 1370 may be manufactured from any biocompatible malleable implant material. In this embodiment, a first passage 1321 located on a proximal end of the ball joint stud member 1320 is sized to accommodate a distal end of a malleable implant 1370. The strut rod 1350 also includes a second passage 1351, opposite the first passage 1321, sized to accommodate a proximal end of the malleable implant 1370. In other embodiments, the malleable implant 1370 may be secured between the static end 1351 of the strut rod 1350 and the ball joint stud member 1320 using other configurations as known to those of skill in the art.

In use, the malleable implant 1370 allows for temporary fixation of the ball joint stud member 1320 within the ball joint body 1310 in a desired position. In this embodiment, the malleable implant 1370 is configured to bend to retain the angled position set by the surgeon with negligible spring-back. The malleable implant 1370 is configured to allow for repeated manipulations without degradation of performance of the malleable implant 1370.

As such, the malleable implant 1370 allows for maintenance of the distal ball joint 1302 in a temporary orientation as set by the surgeon, rather than what is set by gravity, during construction of an external fixation device. The malleable implant 1370 further allows for temporary fixation of the distal ball joint 1302 without the need for external tools to assist in maintenance of the distal ball joint 1302 in the temporary fixed configuration.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

What is claimed is:

1. A polyaxial external fixation strut comprising:
   a strut member;
   a first ball joint coupled to an end portion of the strut member, the first ball joint comprising a first ball joint body; and
   a first ball member, the first ball member being rotatably coupled to the first ball joint body;
   wherein the first ball joint comprises a friction member, wherein the friction member is configured to create friction between the first ball member and the first ball joint body to maintain an adjustable position of the first ball member relative to the first ball joint body;
   wherein the first ball joint further comprises a first ring contact portion and a fixator clip removably attached to the first ball joint body and the first ring contact portion, wherein the fixator clip is configured to fix the first ball joint body and the first ring contact portion in a linear configuration.

2. The polyaxial external fixation strut of claim 1, wherein the strut member further comprises a second ball joint coupled to an end portion of the strut member opposite the first ball joint.

3. The polyaxial external fixation strut of claim 1, wherein the friction member comprises a spring member.

4. The polyaxial external fixation strut of claim 3, wherein the spring member comprises a conical spring washer.

5. The polyaxial external fixation strut of claim 3, wherein the spring member is positioned between an end of the strut member and the first ball member.

6. The polyaxial external fixation strut of claim 1, wherein the friction member comprises a spring clip member.

7. The polyaxial external fixation strut of claim 6, wherein the spring clip member is C-shaped.

8. The polyaxial external fixation strut of claim 6, wherein the spring clip member is configured to at least partially surround the first ball member.

9. The polyaxial external fixation strut of claim 6, wherein the spring clip member is configured to sit within a channel that runs along at least a partial circumference of an inner surface of the first ball joint body.

10. The polyaxial external fixation strut of claim 6, wherein the spring clip member is configured to sit within a channel that runs along at least a partial circumference of the outer surface of the ball member.

11. The polyaxial external fixation strut of claim 1, wherein the first ball first ring contact portion is attached to the first ball member.

12. A polyaxial external fixation strut comprising:
    a strut member;
    a first ball joint coupled to an end portion of the strut member, the first ball joint comprising a first ball joint body;
    a first ball member, the first ball member being rotatably coupled to the first ball joint body; and
    wherein the first ball joint comprises a channel that runs along at least a partial circumference of an inner surface of the first ball joint body or a channel that runs along at least a partial circumference of an outer surface of the first ball member, configured to accommodate a friction member; and
    wherein the friction member is configured to create friction between the first ball member and the first ball joint body to maintain an adjustable position of the first ball member relative to the first ball joint body;
    wherein the first ball joint further comprises a first ring contact portion attached to the first ball member;
    wherein the first ball joint body and the first ring contact portion are configured to be reversibly fixed in a linear configuration.

13. The polyaxial external fixation strut of claim 12, wherein the strut member further comprises a second ball joint coupled to an end portion of the strut member opposite the first ball joint.

14. The polyaxial external fixation strut of claim 12, wherein the friction member comprises a spring clip member.

15. The polyaxial external fixation strut of claim 14, wherein the spring clip member is C-shaped.

16. The polyaxial external fixation strut of claim 15, wherein the spring clip member is configured to sit within the channel that runs along at least a partial circumference of an inner surface of the first ball joint body.

17. The polyaxial external fixation strut of claim 15, wherein the spring clip member is configured to sit within the channel that runs along at least a partial circumference of the outer surface of the ball member.

18. The polyaxial external fixation strut of claim 12, wherein the first ball joint further comprises a fixator clip removably attached to the first ball joint body and the first ring contact portion, wherein the fixator clip is configured to fix the first ball joint body and the first ring contact portion in a linear configuration.

19. A polyaxial external fixation strut comprising:
a strut member;
a first ball joint coupled to an end portion of the strut member, the first ball joint comprising a first ball joint body;
    a first ball member, the first ball member being rotatably coupled to the first ball joint body;
    a first ring contact portion attached to the first ball member; and
    a fixator clip configured to fix the first ball joint body and the first ring contact portion in a linear configuration;
wherein the first ball joint comprises a channel that runs along at least a partial circumference of an inner surface of the first ball joint body configured to accommodate a spring clip member; and
wherein the spring clip member at least partially surrounds the first ball member to maintain an adjustable position of the first ball member relative to the first ball joint body.

20. The external fixation strut of claim 19, wherein the strut housing comprises a second ball joint coupled to an end portion of the strut housing opposite the first ball joint.

21. The polyaxial external fixation strut of claim 19, wherein the spring clip member is C-shaped.

22. The polyaxial external fixation strut of claim 19, wherein the fixator clip is removably attached to the first ball joint body and first ring contact portion.

\* \* \* \* \*